United States Patent

Inoue et al.

[11] Patent Number: 5,990,376
[45] Date of Patent: Nov. 23, 1999

[54] DISPOSABLE ABSORBENT UNDERGARMENT

[75] Inventors: Yasushi Inoue; Kazuaki Onishi; Yasushi Sayama, all of Kagawa-ken, Japan

[73] Assignee: Uni-Charm Corporation, Ehime-ken, Japan

[21] Appl. No.: 09/052,010

[22] Filed: Mar. 31, 1998

[30] Foreign Application Priority Data

Mar. 31, 1997 [JP] Japan .................................... 9-081721

[51] Int. Cl.$^6$ ...................................................... A61F 13/15
[52] U.S. Cl. ........................ 604/378; 604/358; 604/385.1
[58] Field of Search .................................. 604/358, 378, 604/385.1, 385.2, 391; 2/69, 82, 87

[56] References Cited

U.S. PATENT DOCUMENTS 3,110,312  11/1963  Wirth .
5,718,698  2/1998  Dobrin et al. ............................ 604/383
5,772,649  6/1998  Siudzinski ................................ 604/386

Primary Examiner—John G. Weiss
Assistant Examiner—Dennis Ruhl
Attorney, Agent, or Firm—Lowe Hauptman Gopstein Gilman & Berner

[57] ABSTRACT

A disposable absorbent undergarment includes a liquid-permeable topsheet, a liquid-impermeable backsheet and a absorbent core disposed therebetween. The backsheet consists of a breathable plastic film and a breathable fibrous sheet integrally laminated with an outer surface of the breathable plastic film. The breathable fibrous sheet consists of at least a first component layer and a second component layer being in contact with the first component layer. The first component layer has a wettability with body fluids higher than that of the second component layer.

7 Claims, 3 Drawing Sheets

DISPOSABLE ABSORBENT UNDERGARMENT

BACKGROUND OF THE INVENTION

This invention relates generally to a disposable absorbent undergarment and more particularly to such an undergarment such as a disposable diaper, an incontinence pad or pants, or a sanitary napkin or the like.

Many of the conventional disposable diapers each comprising a liquid-permeable topsheet, a liquid-impermeable backsheet and a liquid-absorbent core have usually employed a breathable plastic film as material for the liquid-impermeable backsheet. The disposable diaper has also been proposed which employs the breathable plastic film laminated on an outer surface thereof with a nonwoven fabric as material for the liquid-impermeable backsheet.

The liquid-impermeable backsheet made of the breathable plastic film is preferable since its breathable enables stuffiness possibly generated within the diaper put on the wearer's body to be eliminated or alleviated. However, moisture permeates the backsheet and clings to an outer surface of the backsheet in the form of fine particles of water. These fine particles of water make the outer surface dampish and give a mother with a baby wearing the diaper in her hands an uncomfortable feeling. In addition, the fine particles of water transfer to bedclothes such as a baby dress or a bed sheet and give a baby an uncomfortable wet feeling as if a small amount of urine leaked on the bedclothes.

In the case of the laminate comprising the breathable plastic film and nonwoven fabric used as material for the liquid-impermeable backsheet, the above-mentioned problem of the liquid-impermeable backsheet comprising the breathable plastic film alone is improved to some degree. However, the problem is left unsolved because the nonwoven fabric has not been constructed so as to prevent the moisture from transferring to the outer surface of the backsheet.

SUMMARY OF THE INVENTION

In view of the problem as has been described above, it is a principal object of the invention to create a unique fibrous construction of breathable fibrous sheet such as a nonwoven fabric laminated on the breathable plastic film and thereby to solve the problem.

The object set forth above is achieved, according to the invention, by a disposable absorbent undergarment comprising a liquid-permeable topsheet, a liquid-impermeable backsheet and a liquid-absorbent core disposed between these two sheets, wherein the backsheet comprises breathable plastic film being in contact with the topsheet as well as the absorbent core and a breathable fibrous sheet integrally laminated with an outer surface of the breathable plastic film, wherein:

the breathable fibrous sheet comprises at least a first component layer and a second component layer being in contact with the first component layer and the first component layer has a wettability with body fluids higher than that of the second component layer.

The invention can be implemented in various manners at least as follow: fibers forming the first component layer are at least partially hydrophilic and fibers forming the second component layer are at least partially hydrophobic; the first and second component layers are heat-sealed together; the fibers of the first and second component layers are entangled; the first and second component layers are bonded together by means of intermittently distributed adhesive spots; the second component layer has a plurality of openings; and both the first and second component layers have a plurality of openings.

DESCRIPTION OF THE PREFERRED EMBODIMENTS

Details of a disposable absorbent undergarment according to the invention will be more fully understood from the description of a disposable diaper as an embodiment thereof given hereunder with reference to the accompanying drawings.

Figure 1:
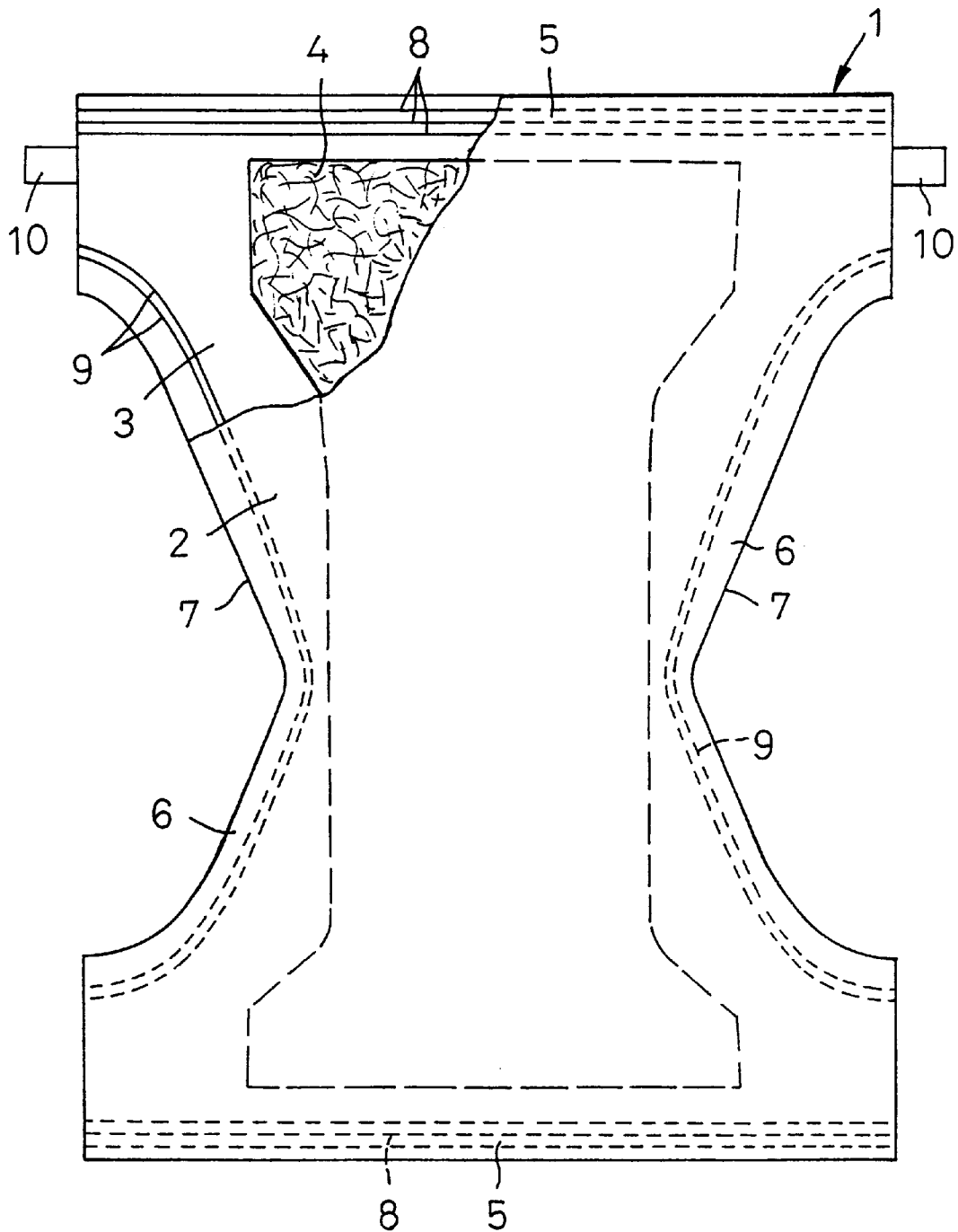
FIG. 1 is a plan view showing a disposable diaper as an embodiment of a disposable absorbent undergarment according to the invention as unfolded and partially broken away.

Referring to FIG. 1, a disposable diaper includes a laminate panel 1 comprising a liquid-permeable topsheet 2, a liquid-impermeable backsheet 3 and a liquid-absorbent core 4 disposed between these two sheets 2, 3. Both the topsheet 2 and the backsheet 3 are dimensioned to extend outward beyond a peripheral edge of the absorbent core 4 by an appropriate width and outward extensions of these sheets 2, 3 form together flexible end flaps 5 and side flaps 6. The transversely opposite side flaps 6 have their outer edges partially cut away except regions in the proximity of longitudinally opposite ends of the laminate panel 1, i.e., regions defining waist-opening so as to be curved inwardly and to define leg-openings' peripheral edges 7. Along the end flaps 5, elastic members 8 for the waist-opening comprising a plurality of elastic threads or ribbon extend between the topsheet 2 and the backsheet 3 and are bonded under an appropriate tension thereto by means of hot melt adhesive (not shown). Similarly, along the leg-openings' edges of the side flaps 6, elastic members 9 for the leg-openings comprising a plurality of elastic threads or ribbon extend between the topsheet 2 and the backsheet 3 and are bonded under an appropriate tension thereto by means of hot melt adhesive (not shown). A pair of tape fasteners 10 of well known art extend outward from transversely opposite side edges of a rear waist region so that the rear waist regions may be connected to a front region by these tape fasteners 10 after the diaper has been put on the wearer's body.

The topsheet 2 may be formed by the conventional material for this component of the disposable diaper, for example, a nonwoven fabric or porous plastic sheet. The absorbent core 4 may be also formed by the conventional material for this component of the disposable diaper, for example, a mixture of fluff pulp and hydrogel having water-insolubility as well as high water absorptivity may be shaped in a panel and top and bottom surfaces thereof may be covered with a water absorptive sheet.

Figure 2:
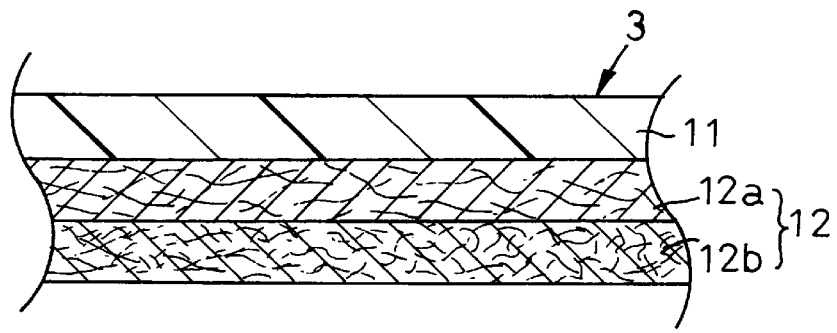
FIG. 2 is a fragmentary sectional view showing a backsheet of the diaper in an enlarged scale.

Referring to FIG. 2, the backsheet 3 comprises a breathable plastic film 11 commonly employed as the backsheet of the conventional disposable diaper and a breathable fibrous sheet 12 integrally laminated on an outer surface of the breathable plastic film 11. The breathable plastic film 11 may be, for example, the film molded from a mixture of polyolefine resin and inorganic material particles and oriented so as to be made porous. This will be apparent to those skilled in the art and no detailed description will be necessary.

Lamination of the breathable plastic film 11 and the breathable fibrous sheet 12 can be achieved by the well known means such as heat-sealing technique or hot melt adhesive, although it is not shown. A manner of bonding may be also selectively in the form of continuous bonding or intermittent bonding.

Figure 3A:
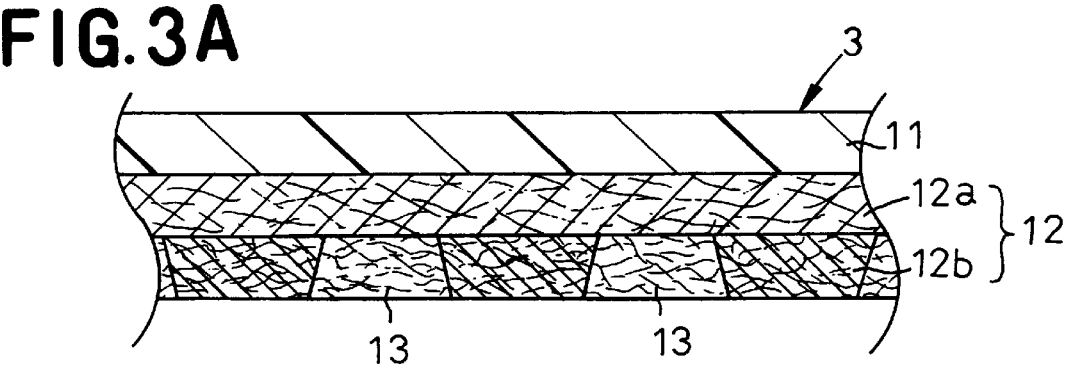
FIG. 3A is a view similar to FIG. 2 showing another embodiment of the backsheet.
Figure 4A:
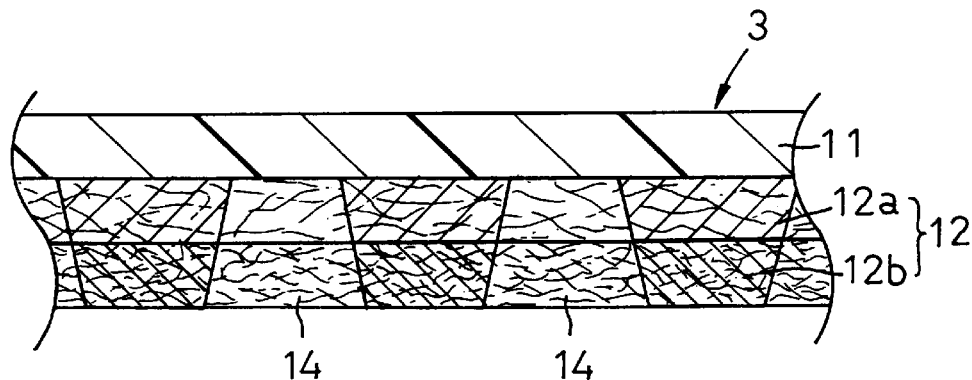
FIG. 4A is a view similar to FIG. 2 showing still another embodiment of the backsheet.

Referring to FIGS. 3(A) and 4(A), the breathable fibrous sheet 12 comprises a first component layer 12a bonded directly to the breathable plastic film 11 and a second component layer 12b bonded to the first component layer 12a. A wettability with body fluids of the first component layer 12a is selected to be higher than that of the second component layer 12b. While not shown, the brethable fibrous sheet 12 may be of three or more layers. The term "wettability with body fluids" should be understood to be such an ability that the first and second component layers 12a, 12b can be wetted with and hold body fluids and/or can absorb body fluids when body fluids come in contact with these layers.

The breathable fibrous sheet 12 generally has a basic weight of 10~45 g/m². The first component layer 12a has a basic weight of 5~20 g/m² and is made of hydrophilic material such as wood pulp fiber, rayon fiber, acetate fiber, cotton fiber or the other hydrophilic synthetic fiber or a combination thereof. The second component layer 12b has a basic weight of 10~25 g/ml and is made of hydrophobic material such a s polyolefine fiber, polyester fiber or polyamide fiber or a combination thereof. The synthetic fiber may be also conjugate fiber of core-sheath type or side-by-side type consisting of a low melting point resin component and a high melting point resin component. The first component layer 12a can be obtained by the well known paper making process so far as this layer substantially comprises wood pulp fiber, e.g., tissue paper. When the first component layer 12a and the second component layer 12b are made of the other fibrous material than the wood pulp fiber, these component layers 12a, 12b are formed by nonwoven fabrics of melt blown, spun laced, needle punched, thermally bonded or chemically bonded fiber. Specific fibrous constructions of the first component layer 12a and the second component layer 12b are selective so far as the former has a wettability with body fluids higher than that of the latter. In other words, the former may contain a certain amount of hydrophobic fiber and the latter may contain a certain amount of hydrophilic fiber so far as the above-mentioned requirement is met. While fineness of the breathable fibrous layer 12 is generally 0.5~12 d, the fiber in the second component layer 12b preferably has a fineness higher than that of the fiber in the first component layer 12a. While the breathable fibrous layer 12 generally has a fibrous density of 0.15~1.5 g/m³, the second component layer 12b preferably has a fibrous density higher than that of the first component layer 12a. By regulating the fineness as well as the density in this manner, it is possible to eliminate any apprehension that the amount of moisture having penetrated the breathable plastic film 11 might penetrate also the second component layer 12b and exude on the outer surface thereof. Consequently, a good feeling to wear the diaper can be obtained.

Bonding of the first component layer 12a and the second component layer 12b may be achieved by any one of the well known methods such as heat-sealing by thermal treatment (inclusive of hot embossing), fiber entangling by water jet treatment or intermittently distributed hot melt adhesive spots.

Figure 3B:
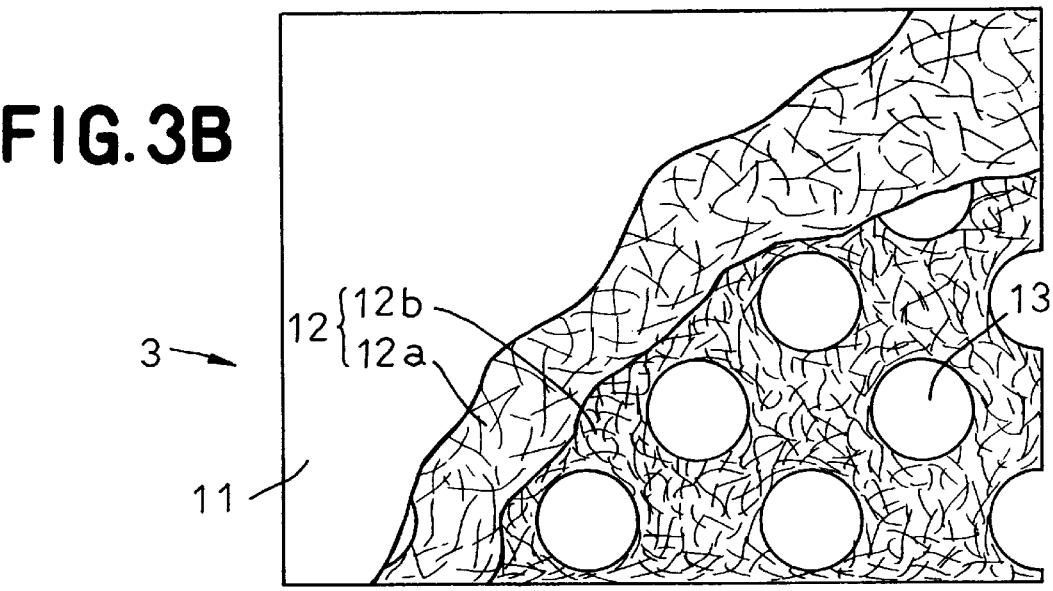
FIG. 3B is a particial plan view showing the backsheet of FIG. 3A.
Figure 4B:
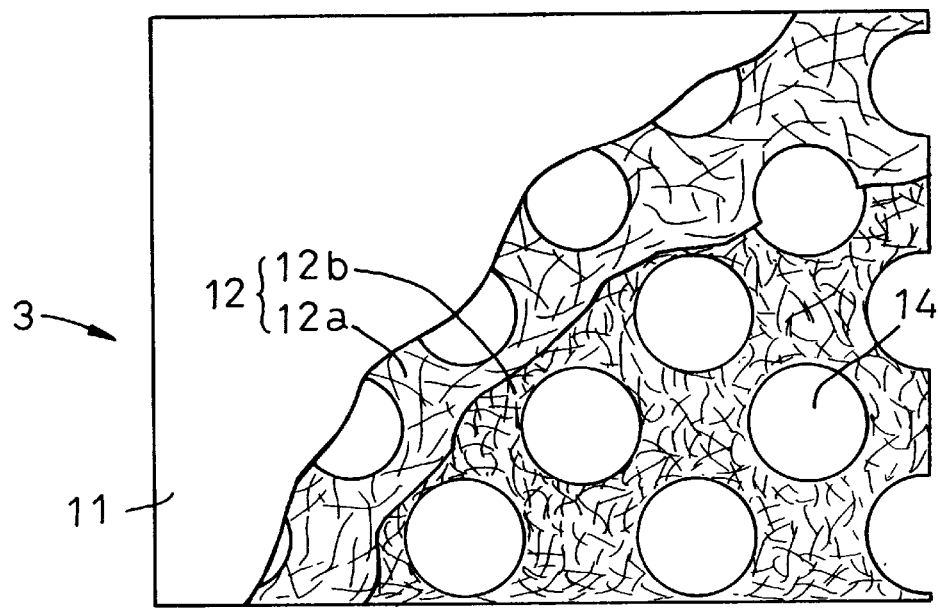
FIG. 4B is a particial plan view showing the backsheet of FIG. 4A.

Referring FIGS. 3B and 4B, the breathable fibrous sheet 12 illustrated by FIG. 3B has independent openings 13 extending through only the second component layer 12b while the breathable fibrous sheet 12 illustrated by FIG. 4B has independent openings 14 extending continuously through both the first and second component layers 12a, 12b. A diameter of each opening 13, 14 as measured on an outer surface (bottom surface as viewed in FIGS. 3B, 4B) of the layer 12 is preferably 0.15~6.0 mm and an area ratio of these openings is preferably 30~70%. By regulating the area ratio in this manner, it is assured that a desired breathability between the interior and the exterior of the undergarment is not significantly affected by the breathability of the breathable plastic film 11 even when the fiber density as well as the interfiber sealing ratio (area ratio) of the breathable fibrous sheet 12 is relatively high.

In the undergarment according to the invention, the breathable fibrous sheet laminated on the breathable plastic film comprises at least the first component layer and the second component layer bonded to the first component layer. The first component layer has a wettability with body fluids higher than that of the second component layer and, in consequence, the amount of moisture having penetrated the breathable plastic film is reliably held or absorbed the first component layer without further penetrating the second component layer and clinging to the outer surface of the breathable fibrous sheet. Therefore, there is neither apprehension that the outer surface of the backsheet (the second component layer) might become moist nor any apprehension that the moisture might transfer to bedclothes such as a baby dress or a bed sheet. In this way, the undergarment according to the invention makes both a baby wearing the diaper and a mother with this baby in her arms free from an uncomfortable feeling.

What is claimed is:

1. A disposable absorbent undergarment comprising a liquid-permeable topsheet, a liquid-impermeable backsheet and a liquid-absorbent core disposed between these two sheets, wherein the backsheet comprises a breathable plastic film being in contact with the topsheet as well as the absorbent core and a breathable fibrous sheet integrally laminated with an outer surface of the breathable plastic film, wherein:

the breathable fibrous sheet comprises at least a first component layer and a second component layer being in contact with the first component layer and the first component layer has a wettability with body fluids higher than that of the second component layer.

2. A disposable absorbent undergarment according to claim 1, wherein fibers forming the first component layer are at least partially hydrophilic and fibers forming the second component layer are at least partially hydrophobic.

3. A disposable absorbent undergarment according to claim 1, wherein the first and second component layers are heat-sealed together.

4. A disposable absorbent undergarment according to claim 1, wherein fibers of the first and second component layers are entangled.

5. A disposable absorbent undergarment according to claim 1, wherein the first and second component layers are bonded together by means of intermittently distributed adhesive spots.

6. A disposable absorbent undergarment according to claim 1, wherein the second component layer has a plurality of openings.

7. A disposable absorbent undergarment according to claim 1, wherein both the first and second component layers have a plurality of openings.

* * * * *